United States Patent
Greppi et al.

(10) Patent No.: US 6,951,542 B2
(45) Date of Patent: Oct. 4, 2005

(54) METHOD AND APPARATUS FOR ULTRASOUND IMAGING OF A BIOPSY NEEDLE OR THE LIKE DURING AN ULTRASOUND IMAGING EXAMINATION

(75) Inventors: Barbara Greppi, Fiesole (IT); Marino Cerofolini, Subbiano (IT)

(73) Assignee: ESAOTE S.p.A., Casala Monferrato (AL) (IT)

(*) Notice: Subject to any disclaimer, the term of this patent is extended or adjusted under 35 U.S.C. 154(b) by 91 days.

(21) Appl. No.: 10/266,549

(22) Filed: Oct. 8, 2002

(65) Prior Publication Data

US 2004/0002653 A1 Jan. 1, 2004

Related U.S. Application Data (63) Continuation-in-part of application No. 10/180,881, filed on Jun. 26, 2002, now abandoned.

(51) Int. Cl.[7] .............................................. A61B 8/00
(52) U.S. Cl. ....................................... 600/443; 600/461
(58) Field of Search .............................. 600/437, 443, 600/447, 458, 459, 461, 471; 128/916

(56) References Cited

U.S. PATENT DOCUMENTS

| | | | | |
|---|---|---|---|---|
| 5,456,257 A | 10/1995 | Johnson et al. | ........ | 128/662.02 |
| 5,497,776 A | 3/1996 | Yamazaki et al. | ..... | 128/660.09 |
| 5,833,613 A | 11/1998 | Averkiou et al. | ........... | 600/440 |
| 5,836,882 A | 11/1998 | Frazin | ........................ | 600/462 |
| 5,928,151 A | 7/1999 | Hossack et al. | ............ | 600/443 |
| 5,951,478 A | 9/1999 | Hwang et al. | .............. | 600/443 |
| 6,048,312 A | 4/2000 | Ishrak et al. | ................. | 600/443 |
| 6,106,473 A | 8/2000 | Violante et al. | ............ | 600/458 |
| 6,146,329 A * | 11/2000 | Hayakawa | .................... | 600/443 |
| 6,485,423 B2 * | 11/2002 | Angelsen et al. | ........... | 600/458 |
| 6,524,247 B2 * | 2/2003 | Zhao et al. | .................. | 600/437 |
| 6,544,178 B1 * | 4/2003 | Grenon et al. | .............. | 600/443 |
| 6,558,328 B2 * | 5/2003 | Rubin et al. | ................. | 600/447 |

FOREIGN PATENT DOCUMENTS

| | | | | |
|---|---|---|---|---|
| EP | 0 278 993 A1 | 8/1988 | ............ | A61B/8/08 |
| EP | 0 357 164 B1 | 3/1990 | ............ | G01S/7/52 |
| EP | 0 952 462 A2 | 10/1999 | ........... | G01S/15/89 |
| WO | WO 96/13213 | 5/1996 | ............ | A61B/8/00 |
| WO | WO 98/43109 | 10/1998 | ............. | G01S/7/52 |

* cited by examiner

*Primary Examiner*—Francis J. Jaworski
(74) *Attorney, Agent, or Firm*—Woodard, Emhardt, Moriarty, McNett & Henry LLP (57) ABSTRACT

A method and apparatus for ultrasound imaging of a biopsy needle or the like during an ultrasound imaging examination, including the steps of alternately performing one or more imaging scans with ultrasound transmit and receive parameters which are adapted for optimized imaging and visualization of the needle and one or more imaging scans with ultrasound transmit and receive parameters adapted for optimized imaging and visualization of the body, in which the needle is inserted, injecting contrast agents in the region to be examined before imaging, and setting ultrasound transmit and receive parameters adapted for optimized imaging and visualization of the body.

37 Claims, 2 Drawing Sheets

METHOD AND APPARATUS FOR ULTRASOUND IMAGING OF A BIOPSY NEEDLE OR THE LIKE DURING AN ULTRASOUND IMAGING EXAMINATION

REFERENCE TO RELATED APPLICATION

The present patent application is a continuation-in-part patent application of U.S. Ser. No. 10/180,881, filed Jun. 26, 2002, now abandoned.

BACKGROUND OF THE INVENTION

The invention relates to a method and apparatus for ultrasound imaging of a biopsy needle or the like during an ultrasound imaging examination, including the steps of alternately performing one or more imaging scans with ultrasound transmit and receive parameters which are adapted for optimized imaging and visualization of the needle and one or more imaging scans with ultrasound transmit and receive parameters adapted for optimized imaging and visualization of the body or details thereof, in which the needle is inserted.

This method is used to monitor the position of a biopsy needle inside the human body, before removing a sample of tissue. The needle and the surrounding tissue are imaged in real time for an easier control of the needle orientation and proper depth, to remove the tissue from the predetermined location. Obviously, the best position of the needle is the one in which both the instrument and the tissue are best imaged. Unfortunately, the tissue and the instrument are reflectors having totally different characteristics, which require different settings of ultrasound imaging parameters. This is also due to the fact that the needle is a specular reflector, i.e. reflects ultrasonic waves like a mirror. Hence, as the distance from the ultrasound beam incident on the needle to the perpendicular of the needle increases, the energy reflected toward the probe decreases. Nevertheless, these conditions contrast with the optimized setting conditions for tissue imaging.

U.S. Pat. No. 5,836,882 discloses a method and an apparatus for localizing a tip of a probe inside a biotic structure. The apparatus includes a probe with an ultrasonic transmitter attached proximate a tip of an insertion end of the probe. The apparatus further includes a color doppler ultrasonic imaging system coupled to a sonifying transducer and a speaker coupled to the ultrasonic imaging system which reproduces sound information indicative of a position of the probe relative to the sonifying transducer.

EP 0 278 993 deals with a concentric biopsy probe. An ultrasound imaging probe suitable for concentric on-axis biopsy procedures includes an aperture through which a biopsy needle is inserted to sample a target tissue previously located by the ultrasound probe. In operation the ultrasonic probe is first positioned on the subject over target tissue A cursor is moved to visually overlap the target tissue within the subject, an the depth is indicated on a corresponding display. A biopsy needle is selected and adjusted to extend to the indicated depth when inserted through the ultrasonic probe and transducer aperture into the subject. Thus the apparatus provides for the source aperture, used for imaging, thus minimizing risk and error arising from conventional off-axis needle entrances.

U.S. Pat. No. 6,048,312 and EP 952,462 disclose methods and apparatuses which allow imaging of the needle and tissue during an ultrasound imaging session. According to the methods disclosed in these documents imaging is performed in the B-mode or Doppler or Color Doppler modes, wherein the ultrasound beam firing parameters are alternately modified for optimized imaging of the needle and of surrounding tissues. Then, the images acquired thereby are combined to obtain a single image in which the needle and the surrounding body are both displayed.

While tissue imaging parameters are well-known and widely used, the above documents suggest that the needle is imaged by suitably deforming or steering the beam transmitted by a probe, which is particularly linear, so that the angle of incidence between the beam and the needle is perpendicular to the needle or as close as possible to this condition. The two above mentioned documents are to be intended as parts of the following disclosure, even as an explanation of the detailed technical aspects of this invention.

However, it often happens that the tissue wherefrom a sample is to be removed, for instance a cyst or tumor tissue, is characterized by an increased circulation, i.e. by an increased blood flow thereto. Therefore, there is an interest in imaging body fluid flows, particularly vascular flows, rather than static tissues. Unfortunately, body fluids have such characteristics that they cannot be easily displayed by using traditional ultrasound imaging techniques. Body fluids are worse reflectors as compared with static tissues, hence their imaging contribution is several orders of magnitude smaller than that of static tissues, i.e. body flows are essentially anechogenic, whereas static tissues are echogenic or hyperechogenic. Hence, specific techniques have been developed to allow selective optimized imaging of body fluid flows as opposed to static tissues, which techniques are divided into two main branches. Invasive techniques are those in which contrast agents are injected in the region under examination, i.e. agents consisting of microbubbles which are carried by body flows and have a non linear reflection behavior, i.e. reflect the ultrasound beams, which have been transmitted at a certain fundamental frequency, at a harmonic or sub-harmonic of the fundamental frequency of the ultrasound beams transmitted to the body under examination. In this case, since static tissues have a linear reflection behavior, by only detecting the beams reflected at a selected harmonic or sub-harmonic frequency the imaging contribution of body fluids may be differentiated and isolated. Here, the transmit and receive parameters are still different from those required for optimized imaging of the needle and the static tissues surrounding it.

An alternative fluid flow imaging technique consists in using the phase shift introduced in the reflected beams by body fluids with respect to static tissues. In fact, the particles which form body fluids are in motion, unlike the particles of essentially static tissues, and determine a phase shift between the reflected beams and the incident beams, whereas essentially no phase shift occurs for beams reflected by static or quasi static tissues. Hence, by providing two successive imaging procedures, with identical transmit and receive parameters, and by directly subtracting the received signals of the two imaging procedures, imaging contributions having the same phase are removed or drastically reduced, whereas all imaging contributions which have had a phase shift are maintained.

Hence, the transmit and receive parameters for body flow imaging are different from those optimized for imaging the needle and the surrounding tissues, both as regards the imaging frequency and the imaging method and as regards the transmission intensity of the ultrasound beams for illuminating the body under examination. In fact, it is known that, in order to avoid the mechanical collapse of contrast agent microbubbles, the intensity of incident ultrasound beams has to be reduced to limit the mechanical index and control or prevent as much as possible the collapse of contrast agents.

The techniques disclosed by U.S. Pat. No. 6,048,312 and EP 952,462 do not address the need to not only monitor the needle and the surrounding tissue but also body fluid flows for a proper and more accurate location of the biopsy site position, and do not even disclose a method to do this and an apparatus for implementing the method, especially allowing real time imaging. The real time imaging feature should not be underestimated, since the patient is in an invasive treatment condition, with a needle inserted in his/her body, and the removal operation has to be as fast as possible to avoid any trouble or other inconvenience.

Therefore, the invention has the object of providing a method and an apparatus for ultrasound imaging of a biopsy needle or the like, which provides a higher capability for an optimized imaging of the needle and of the body in which the latter is inserted.

The invention achieves the above purposes by providing a method and an apparatus for ultrasound imaging of a biopsy needle or the like, during an ultrasound imaging examination as described hereinbefore, which includes the step of injecting contrast agents in the region under examination, and in which the ultrasound transmit and receive parameters adapted to optimized imaging and display of the body or details thereof, in which the needle is inserted, are parameters optimized for imaging body fluid flows.

Particularly, the ultrasound transmit and receive parameters optimized for imaging fluid flows involve the transmission of ultrasound beams at the fundamental frequency and with a low mechanical index, i.e. at a low intensity and the reception of ultrasound reflected beams at a harmonic or sub-harmonic frequency, particularly at the second harmonic of the fundamental frequency of transmitted beams.

In combination with the above, the invention provides alternate ultrasound imaging with transmit and receive parameters optimized for imaging the needle, with transmit and receive parameters optimized for imaging the tissues of the body under examination or a detail thereof, and with transmit and receive parameters optimized for imaging body fluid flows.

It shall be noted that alternate imaging is intended to mean that, within the same section of the imaged body, one or more images or frames are respectively acquired for transmit and receive parameters optimized for imaging the needle, tissues, or body fluid flows. Here, it is possible to properly account for the transmit beam firing repetition times.

The images obtained by the above imaging procedures with transmit and receive parameters optimized for imaging the needle or body fluids and possibly for tissues may be displayed with well-known techniques, i.e. by assigning different color scales and/or gray scales to the intensity values of the reflected beams, and by combining the images together, i.e. by overlaying the different images of the needle, the body flows and/or possibly tissues.

As an alternative thereto, images may be displayed in adjacent and separate positions or with different image sub-combinations, such as a combination of images of the needle and of tissues in adjacent positions, and a combination of images of the needle and of body fluid flows, or other possible sub-combinations.

According to an embodiment of the method, the invention provides an imaging procedure with a low mechanical index and at the second harmonic for imaging body fluid flows and an imaging procedure with a low mechanical index and at the fundamental frequency with needle optimized parameters, for instance by using a steering technology in the case of linear probes.

An alternative embodiment provides an imaging procedure with a low mechanical index and at the second harmonic for imaging body fluid flows and an imaging procedure with a high mechanical index and at the fundamental frequency with needle optimized parameters, for instance by using a steering technology in the case of linear probes.

Another alternative embodiment provides an imaging procedure with a low mechanical index and at the second harmonic for imaging body fluid flows and an imaging procedure with a high mechanical index and at the fundamental frequency, with needle optimized parameters, for instance by using a steering technology in the case of linear probes, as well as an imaging procedure with a high mechanical index and at the fundamental frequency with tissue optimized parameters.

Yet another alternative embodiment provides an imaging procedure with a low mechanical index and at the second harmonic for imaging body fluid flows and an imaging procedure with a high or low mechanical index and at the fundamental frequency, with needle optimized parameters for instance by using a proper steering technique in the case of linear probes, as well as an imaging procedure with a high mechanical index and at the second harmonic frequency, with tissue optimized parameters.

A variant embodiment provides an imaging procedure at the second harmonic optimized for imaging body fluid flows and an imaging procedure with a high or low mechanical index and at a fundamental or second harmonic frequency, which subtracts two successive reflection echoes determined by two successively fired ultrasound beams with the same parameters, for imaging the needle.

The different imaging procedures may be executed alternately, within a predetermined frame rate, or parallel to each other, i.e. simultaneously at least as regards processing, there being provided two or three dedicated receive and processing chains.

The different variant embodiment as disclosed above may be provided in combination with three-dimensional imaging methods.

Particularly, a preferred three-dimensional imaging method includes the following steps:

transmitting ultrasound beams, generated by transducers, into a volume under examination, corresponding to a body under examination or a part thereof; receiving and storing the signals generated by the ultrasound beams in said volume under examination; processing the received signals into image data associated to image dots or lines of a display; displaying at least a portion of image data on the display according to user selected parameters, relating to a predetermined image section or projection plane of said volume under examination, the processing of ultrasound beams and/or the display being predetermined in a targeted manner, with reference to a previous selection of an image section or projection plane of the volume under examination to be imaged and which method comprises the additional steps, i.e.:

defining a virtual volume which coincides with the body or the part thereof under examination or a three-dimensional reference system, which have a precise orientation with respect to the scan planes generated by the ultrasonic probe; selecting the section plane of the body under examination and/or of the part thereof along which ultrasonic imaging is to be performed; determining the coordinates of the dots which form said section plane along which imaging is to be performed with reference to the virtual volume; limiting the scan to the area which coincides with said section plane along which imaging is to be performed; transmitting and receiving transmit signals and reflection echoes, only relating to the lines of view of the probe which coincide with the projection surface or band of the selected section plane along which imaging is to be performed; processing and displaying only the received echo signals.

As shown above, the method involves the combined display of the images acquired by optimized imaging for the needle, body fluid flows and/or possibly for tissues. Further, the different images may be appropriately colored in a desired manner to allow an optimized interpretation by the personnel charged with diagnostic evaluation.

The method of the invention provides alternate and successive transmission of ultrasound beams with parameters optimized for imaging the needle, body fluid flows and/or possibly tissues respectively according to the above disclosure and parallel processing of the received data, and has one, two or possibly three separate processing chains, which are set for receiving and processing the echoes deriving from the two or possibly three types of parameters of the transmitted ultrasound beams.

In this case, the parameters which control the optimized transmission for imaging the needle, body fluid flows and/or stationary tissues may be contained in a memory of the apparatus.

Hence, the method provides the automatic modification of the transmit parameters based on the number of scans of the region under examination assigned to optimized imaging of the needle, of fluids and/or of tissues respectively.

The number of images to be acquired alternately with the specific optimization for the needle, for fluid flows and/or possibly for tissues may be obviously selected.

Specific receiving, processing and storing chains, or a single chain which rapidly switches its characteristics for the various scan modes are enabled in a synchronized manner with the transmission of ultrasound beams having the specific optimized parameters for the needle, the fluid flows and/or possibly for tissues. The images obtained thereby may be then processed and possibly combined together in any manner, to be further displayed and/or stored.

As an alternative, transmit parameters may be set in a memory and later recalled from the memory, in a manner that corresponds to the specific preset succession of scans, to control the scan according to the different parameters contained in the memory.

An additional variant embodiment provides memories both for transmit parameters and for receive parameters and possibly even for image processing and/or handling and combining parameters.

In this case, each specific setting of transmit parameters, univocally related to imaging optimized for the needle, body fluid flows and/or possibly tissues corresponds to a specific setting of control parameters for the processing chain and possibly to a specific setting of parameters for processing, handling and/or combining the images obtained with different modes for the needle, body fluid flows and/or possibly tissues.

The invention also relates to an apparatus for the implementation of said method, which comprises an ultrasonic probe, means for generating ultrasound beams and for controlling the scan of a body under examination by said ultrasound beams; means for receiving and reconstructing image data from the ultrasound beams reflected by the body under examination and display means, said apparatus being further provided with a memory in which the parameters for generating the ultrasound beams and for scanning the body under examination or a part thereof are loaded, which parameters are alternately optimized for imaging the needle and/or body fluid flows and/or possibly tissues, and means for receiving, reconstructing and processing reflected ultrasound beams deriving from said transmit beams, in a manner which is related to the parameters and scan modes with the transmitted ultrasound beams.

Advantageously, the apparatus includes a single chain for generating the ultrasound beams transmitted toward the body under examination or a part thereof, wherein the optimization of imaging parameters is controlled by means provided with a parameter setting memory, which is enabled according to enabling schedules which provide alternate scans with the different parameters.

In combination with the above, the apparatus includes one or more receive and processing chains, each dedicated to the simultaneous or successive handling of the data obtained by any type of imaging parameters.

In accordance with a variant embodiment, the apparatus includes a single chain for generating the ultrasound beams to be transmitted and/or for scanning and a single chain for receiving and processing, there being provided a central control unit, which is connected to the memories containing the parameters of transmitted ultrasound beams according to the different optimizations for imaging the needle and body fluid flows and/or possibly tissues, and to the memories containing the receive and processing modes dedicated to the reflection signals obtained with the particular optimized settings of parameters for imaging the needle and/or body fluid flows and/or possibly tissues, which control means access the memories according to an imaging time protocol based on the different parameters and, as a result, control the means for generating and transmitting the ultrasound beams, as well as the means for receiving, processing and/or handling images and/or possibly combining the individual images optimized for the needle and/or body fluid flows and/or possibly tissues.

The advantages of this invention are self-evident from the above disclosure and especially consist in allowing an optimized visualization of a biopsy needle in combination with an optimized display of body fluid flows and possibly of the tissues around the needle.

The whole is obtained in a fast manner, such as to allow real-time imaging, without imposing long waiting times on patients, and while maintaining short intervention times.

The better visualization of the biopsy needle and of fluid flows and/or tissues allows a more accurate positioning of the needle in the sample removal site, thereby ensuring a better reliability of diagnostic tests performed thereon, particularly when the sample removal site has a very small size, and tissue removal might easily occur outside it.

The visualization of body fluid flows allows a more accurate identification of the tissues of interest for sample removal, particularly in not completely degenerated conditions, or in initial stages of diseases like tumors or the like.

The possibility to combine the methods of the invention with other imaging methods, like three-dimensional imaging methods, or other methods, provides a maximized expansion and improvement flexibility.

Further improvements of the method and of the apparatus will form the subject of the subclaims.

The characteristics of the invention and the advantages derived therefrom will appear more clearly from the following description of a few non limiting embodiments.

SUMMARY

A method and apparatus for ultrasound imaging of a biopsy needle or the like during an ultrasound imaging examination according to one embodiment of the present invention comprises the steps of first alternately performing one or more imaging scans with ultrasound transmit and receive parameters which are adapted for optimized imaging and visualization of the needle and one or more imaging scans with ultrasound transmit and receive parameters adapted for optimized imaging and visualization of the body or details thereof in which the needle is inserted, next injecting contrast agents in the region to be examined before imaging and setting ultrasound transmit and receive parameters adapted for optimized imaging and visualization of the body or details thereof wherein the needle is inserted, so that these parameters are optimized for imaging body fluid flows.

One object of the present invention is to provide an improved method and apparatus for ultrasound imaging of a biopsy needle or the like.

Related objects and advantages of the present invention will be apparent from the following description.

DESCRIPTION OF THE PREFERRED EMBODIMENT

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 1:
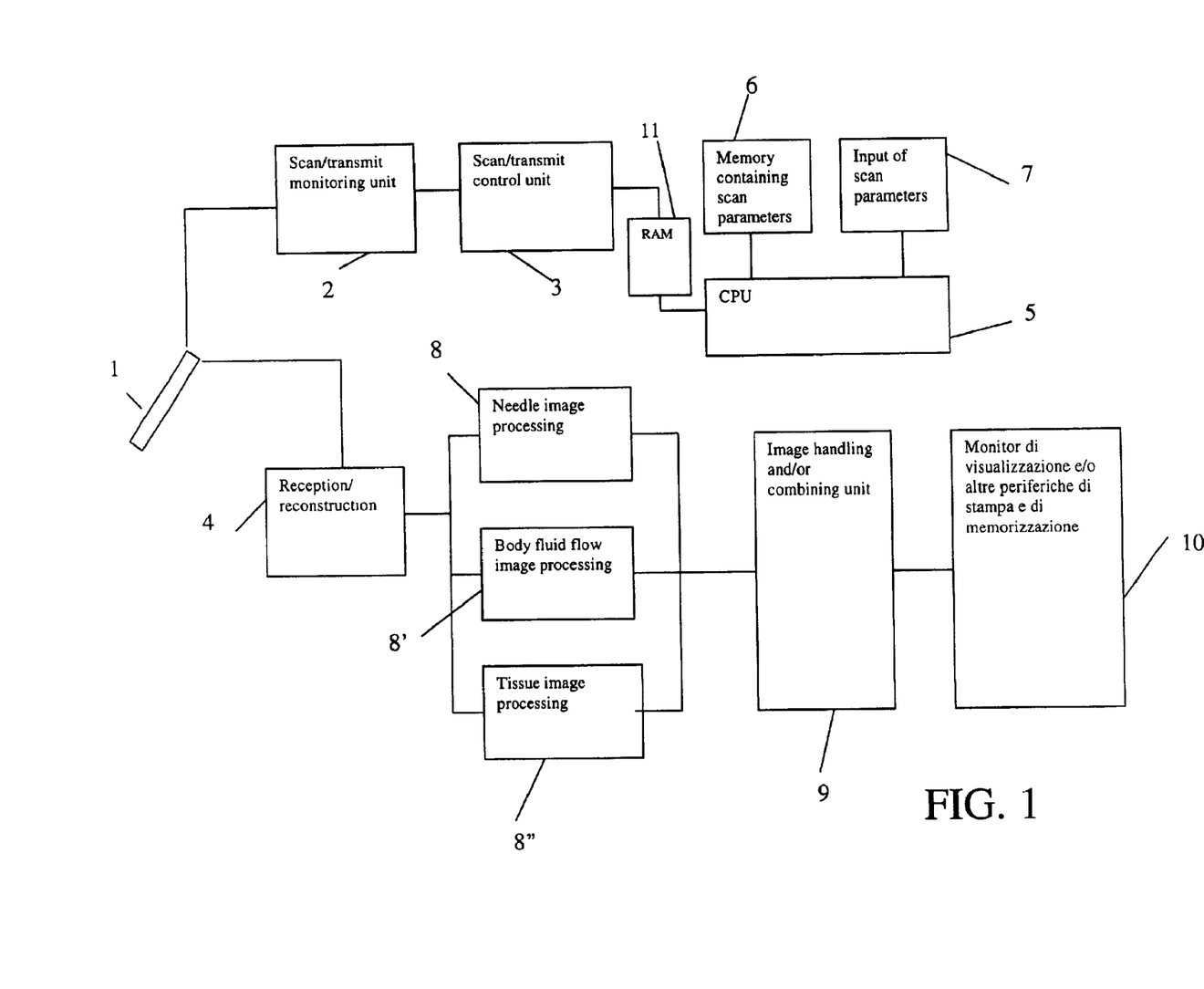
FIG. 1 shows a first embodiment of an ultrasound imaging apparatus according to the invention.
Figure 2:
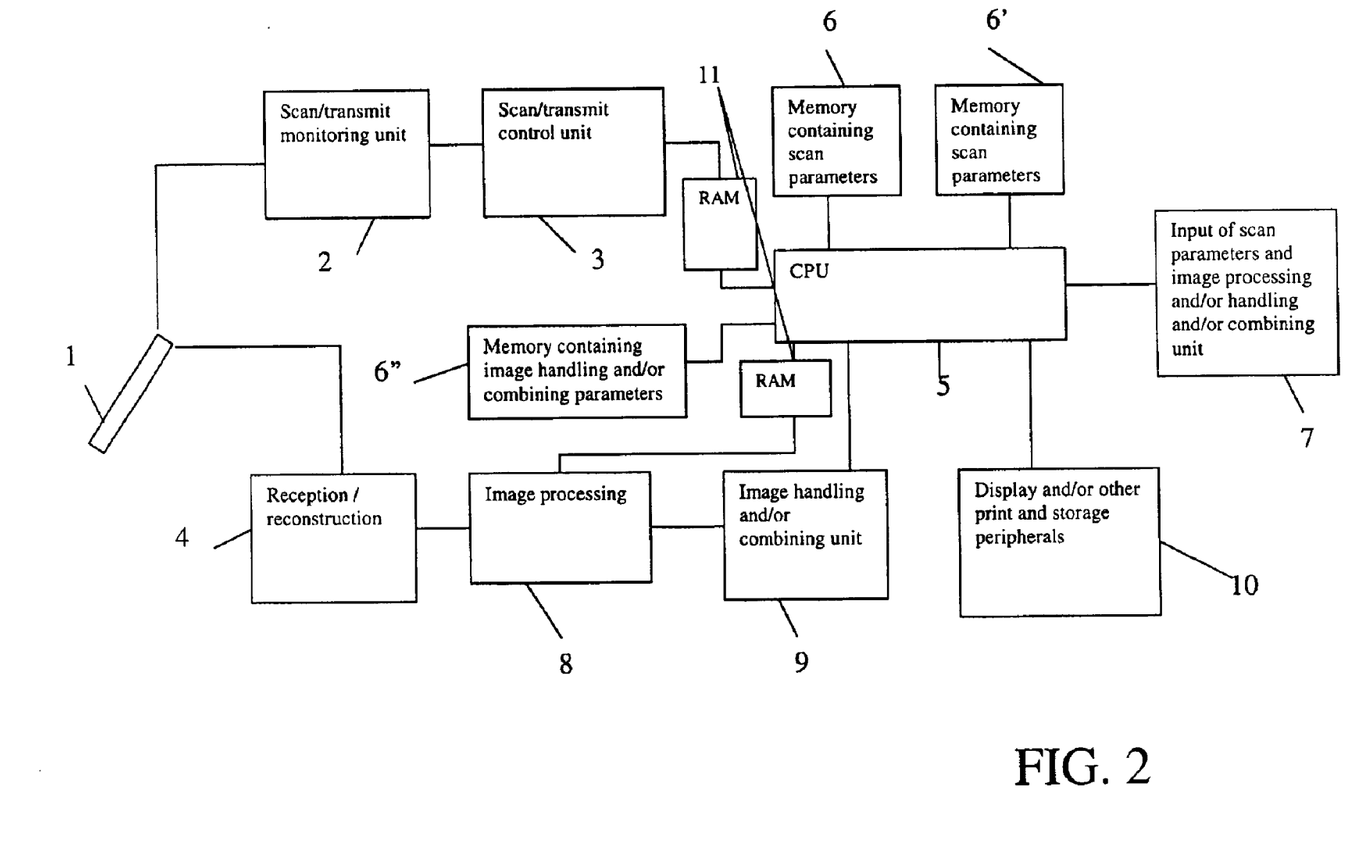
FIG. 2 shows a second embodiment of an ultrasound imaging apparatus according to the invention.

Referring to the figures, a block diagram is shown of two embodiments of an apparatus particularly adapted for implementing the method of the invention.

The steps of the method of the invention allow imaging with parameters optimized for imaging a biopsy needle or similar instrument and for imaging body fluid flows with the help of contrast agents.

In this case, besides the injection of contrast agents in the region under examination, a succession of ultrasound imaging scans of the region of interest is performed within the biopsy procedure, i.e. from the insertion of the biopsy needle to the position in which the tissue sample removing means are in the predetermined removal site, through the removal of the tissue sample and possibly to the extraction of the needle, whereby the needle and the body fluid flows are imaged in the region in which the needle is introduced and particularly in the intervention area thereof. For an optimized ultrasound imaging of the needle and body fluid flows, imaging is performed with transmit and receive parameters specifically optimized for imaging the needle and for imaging fluid flows.

Since the needle is a specular and highly echogenic reflector, the transmitted ultrasound beams must be oriented perpendicular to it. Also, since it has a quasi linear response, hence with a low harmonic content, it requires the received signal to be processed at the transmit fundamental frequency. However, fluid flows are anechogenic, hence they are highlighted by the use of contrast agents which, due to their non linearity, require the reflected beams to be received at a harmonic or sub-harmonic of the transmit fundamental frequency, generally at the second harmonic frequency. At this frequency, the needle does not give any significant contribution and may be imaged with a sufficient clearness or accuracy.

Therefore, within a biopsy session, the method of the invention provides alternate imaging with ultrasound beam transmit parameters and with corresponding receive and processing parameters that are optimized for imaging the biopsy needle and the fluid flows respectively.

For ultrasound imaging of the needle, any known mode may be used amongst. B-Mode, Doppler, Color Flow Mapping and other non conventional modes such as Pulse Subtraction, which forms the subject of a former Italian application SV2000A00018 by the owner thereof, and two-dimensional and three-dimensional imaging modes like those described in U.S. Pat. No. 5,928,151, U.S. Pat. No. 5,497,776, WO 98/43109.

The imaging mode as described in the application SV2000A00018 is an ultrasound imaging method, particularly of moving bodies, tissues, flows, or the like, which includes the following steps:

periodically emitting ultrasonic pulses along a predetermined view line and with a predetermined repetition rate through one or more transducers;

receiving the echoes produced by the body and/or the tissues or flows and transforming them into echo signals;

processing echo signals for data extraction and for image generation based on this data, by determining a real time vector difference between the echo signals of two pulses successively emitted at predetermined time intervals and by using said difference signal as an information signal for ultrasound imaging. In order to extract an signal which is useful for imaging, a maximum and/or minimum threshold is set for filtering the difference signal between two successive echo signals, to neutralize signal flashes generated by any relative micromotion between the probe and the echogenic or hyperechogenic tissues surrounding the flows whereof ultrasonic imaging is desired. Said thresholds allow to image the high intensity signal part that is generated by the needle, based on their settings. However, the fluid flow signal part has a definitely lower intensity as compared to the needle-related received signals. By also setting intermediate thresholds the component of the received signal generated by tissues may be also imaged by extracting the signal part delimited by the intermediate thresholds.

Body fluid flows are imaged with the help of contrast agents by traditional modes like Harmonic Imaging, and any well-known variant and improvement to this mode may be used, e.g. any filtering arrangement, the so-called Pulse Inversion technique as described, for instance, in U.S. Pat. No. 5,833,613, U.S. Pat. No. 5,951,478, U.S. Pat. No. 5,456,257, EP 0357 164 and WO 96/13213 which are expressly incorporated by reference herein.

In accordance with an improvement, a third imaging procedure may be provided as an alternative to the two above procedures, whereby stationary or essentially stationary tissues are imaged in the region of interest. Here again any prior art body tissue imaging technique may be selected, and imaging parameters are again optimized to obtain optimal images.

The images obtained thereby, successively and alternately to each other may be combined into a single image or in sub-combinations of two or more images optimized for imaging the individual devices.

An imaging example of the invention consists in obtaining one or more successive section images of the region under examination with parameters optimized for imaging the needle, then one or more successive section images of the region under examination with parameters optimized for imaging body fluid flows and possibly, a succession of one or more section images with parameters optimized for imaging static tissues.

The images acquired with the different optimization parameters may be combined in any alternate manner, e.g. it is possible to reduce the number of images acquired with parameters optimized for imaging tissues, as compared to the images acquired with parameters optimized for imaging the needle and/or for imaging body fluid flows.

With reference to FIG. 1, an ultrasound imaging apparatus adapted for implementing the method of the invention comprises an ultrasonic probe 1, which has an array of transducers in different configurations, e.g. a row of adjacent transducers or a two-dimensional matrix of transducers or an array of transducers disposed on one row or more adjacent rows, which transducer array may be translated and/or rotated in such a manner that an ultrasonic pulse beam may be focused along adjacent lines of view, which form together a section plane or a section band or slice.

When the transducer array is of the displaceable or rotatable type, a plurality of section planes of the body under examination or of section bands or slices of the body under examination may be scanned, in a fan-like arrangement over the region under examination.

Piezoelectric transducers are adapted to turn electric excitation signals into ultrasonic waves having a predetermined frequency and to turn the received ultrasonic waves into electric signals.

The transducers of the array are controlled by a scan and transmit monitoring unit 2, which is in turn controlled by a scan and transmit control unit 3. This unit is controlled by a CPU 5, which is connected to a memory 6 containing the different imaging parameters for the different optimized modes for imaging the needle, body fluid flows and/or tissues. Moreover, the memory also contains imaging mode information, e.g. relating to B-Mode, Doppler, Power Doppler, Color Doppler, Harmonic Imaging, Pulse inversion, Pulse subtraction and others to be associated to the different parameters.

These parameters and beam setting data may be inserted in the memory through data input means 7 which are connected to the CPU and may be of any type, such as magnetic card or chipcard readers, floppy disk drives, bar code readers, etc.

The modes for performing scans with the different optimized parameters are also set in the memory 6, with reference to their execution in time, i.e. an alternate execution protocol in time, with the different optimized combinations of parameters.

A unit 4 for receiving/reconstructing reflected echo signals is also connected to the transducers, and transmits data to one of the three different processing sections 8, 8', 8", each specifically dedicated to the processing of echo signals generated by a scan with the particular optimized parameters and with the imaging modes associated thereto. Obviously, the one or the other processing unit is enabled in synchronism with the protocol for timed execution of the different optimized scans.

Based on an alternate execution protocol with the different optimized parameters, the CPU transmits the settings of scan parameters, such as frequency, focusing type, mechanical index, imaging mode, from the memory 6 to the scan and transmit control unit 3.

The scan and transmit control unit 2 generates the pulses for exciting the transducers having appropriately selected frequency, focusing rule, and mechanical indexes based on the combination of parameters optimized for imaging the needle, body fluid flows and tissues respectively.

Reflection echoes are received by the transducers, which reconstruct a set of reflection data in the receiving and reconstructing unit 4, which in turn sorts the information received in time into space distribution information with reference to each focusing line of the ultrasound beams. The data so reconstructed are transmitted to the units 8, 8', 8", each dedicated to a different processing mode and controlled by the same parameters that control scan/transmission.

The image data processed thereby and corresponding to a data matrix, with data univocally related to image dots with predetermined positions in space is then changed into signals for controlling a display, i.e. into a virtual image in the image handling and combining unit 9.

The virtual image signals so generated are displayed and/or stored according to different modes and in any desired unit 10, e.g. a display, a printer, fixed storage media like hard disks and/or on removable and portable storage media like floppy disks and other similar media.

The unit 9 may be also used to combine the different images acquired by optimized scans for imaging the needle, body fluid flows and/or static tissues. Any type of combination or sub-combination may be provided. For instance, three individual, separate images may be visualized in the display 10, each deriving from the optimized scan for imaging the needle, body fluid flows and tissues. As an alternative thereto or in combination therewith, an image may be displayed which is formed by overlaying said three images or only two of these three images or two or three images, each obtained by overlaying only two different images of the three possible combinations.

The unit 10 may also allow the optimized images to be colored, particularly for highlighting the needle, body fluid flows or tissues. One of the many possible combinations consists in providing the needle with a color which contrasts with the colors of fluid flows. Moreover, the different speeds of fluid flows may be possibly highlighted by using a scale of different color tones within the same color or different colors, in contrast with the one assigned to the needle. The surrounding and essentially stationary tissue may be imaged by using a gray scale. The methods of assigning a color tone scale or a gray scale are well-known and widely used in the field of diagnostic imaging, even with non ultrasound imaging techniques. Therefore, the example of FIG. 1 consists in an ultrasound imaging apparatus, providing at least two, possibly three parallel chains for processing the received signals which may be also operated at the same time.

FIG. 2 shows a variant embodiment, which provides a single image processing chain 8"" and an image handling and combining unit 10, which may be both controlled and set by the CPU 5, based on sets or combinations of parameters contained in the memories 6', 6". In this case, the operation is such that the CPU extracts from the memories 6', 6" the combinations of image processing and handling and/or combining parameters corresponding to the combinations of parameters used for scanning. This is made in synchronism with the timed scan protocol to execute scans with the different optimizations for imaging the needle, fluid flows and tissues, so as to ensure that the received echo signals are processed according to the parameters for generating the transmitted ultrasound beams, which generated the echoes and with the scan modes that were used upon transmission.

As is apparent, the apparatus according to the variant of FIG. 2 provides highly flexible setting capabilities, since the optimized settings may be modified, through data input means 7, both upon transmission and upon reception, as well as for display.

With reference to an improvement of the invention, a working storage memory may be provided both in the embodiment of FIG. 1 and in the one of FIG. 2, directly accessed by the scan and transmit control unit 2 and the processing unit 4 and/or the image handling and combining unit 9. This working storage memory, denoted as 11, allows to load different optimized parameters for imaging the needle, body fluid flows and/or possibly tissues for direct access thereof by said units, whereby the CPU 5 does not have to extract these parameters every time from the memory 6 or the additional memories 6' and 6", and reprogram the apparatus, with considerable time savings in scanning, processing and displaying operations. The working storage memory 11, here a RAM memory, may be also loaded with modes for controlling three-dimensional scan which is integrated in the apparatus, when a swinging transducer probe is provided, and does not require the help of position sensors outside the probe. The provision of a working storage memory provides faster scan and acquisition functions, which are controlled directly by the ultrasound imaging apparatus and faster and more efficient transitions between several scan planes and possibly between scanning, image processing and/or handling and displaying modes.

The high flexibility of the apparatus as described above allows to provide several different scan modes, optimized for imaging the needle, fluid flows and possibly tissues, whereof a few examples are listed below:

EXAMPLE I

The needle and fluid flows are respectively imaged by a scan at the fundamental frequency with a technique selected among Bmode, Doppler mode, Color Flow Mapping or other known techniques, and a scan at the second harmonic and with a low mechanical index, which is used to image contrast agents, previously injected in the region under examination, by extracting second harmonic signals by means of filtering processes or by the so-called Pulse Inversion technique or other well-known techniques.

EXAMPLE II

Fluid flows are imaged in an optimized manner by a scan at the second harmonic and with a low mechanical index, which is alternated to a scan with a high or low mechanical index and at the fundamental frequency. Further, in combination with the use of linear probes, in which the transducers are disposed in a row, the transmitted beams may be steered to orient the incident beams with angles as close as possible to the orthogonal axis of the needle.

EXAMPLE III

Fluid flows are imaged in the optimized manner, by a scan at the second harmonic and with a low mechanical index, alternated to an scan optimized for imaging the needle, with a high or low mechanical index, at the fundamental frequency, and with linear probes, with beams being steered to orient incident beams with angles as close as possible to the orthogonal axis of the needle, and to a scan for optimized imaging of static tissues, with a high mechanical index and at the fundamental frequency.

The different optimized scans may be performed within the same section plane of the region under examination or be limited to a few frames or to individual frames obtained by the different modes as mentioned above. The different optimized scans might be also performed on different adjacent section planes.

A variant embodiment provides the use of an imaging technique as described above with reference to the patent application SV2000A000018, by the owner hereof, in which two identical ultrasonic pulses are transmitted, for further subtraction of the reflection echoes thereof. This imaging technique, when combined with second harmonic imaging allows to obtain, by simply setting thresholds and differentiated processing, an optimized image for body fluid flows and an optimized image for the needle. In fact, upon further subtraction of the two echoes, the signals related to static image components are elided, and the signals related to moving parts remain. In this case, by providing a processing chain for second harmonic signals and by appropriately filtering all contributions above a certain intensity threshold, image data optimized for fluid flows are obtained, whereas optimized needle images are obtained by removing the signals of the echo difference below a certain threshold and by maintaining and processing the signals above a certain threshold.

The movement of the biopsy needle provides very high contributions in terms of difference signals between two successive echoes, whereas the contributions of body fluid flows and/or static tissues are low, much lower than those of the needle. Therefore, the provision of an intensity threshold and the decision to process in different manners the lower and the upper portions of the echo difference signal allows an independent and optimized control of the image of body fluid flows and the image of the needle.

As an alternative to what has been disclosed in the above examples, it is possible not to limit the mechanical index of the transmitted beams for second harmonic imaging, and to keep it high to destroy the microbubbles of contrast agents.

The method of the invention may be also provided in combination with three-dimensional scan techniques of any type.

These techniques provide the scan of a succession of two-dimensional section images which are further stored in succession and with univocal spatial references, whereby a virtual image may be obtained which is composed of a plurality of image unit volumes, the so-called voxels. In this case, any known technique may be used, e.g. manual displacement of the probe in combination with position and orientation sensors, for instance of the magnetic, mechanical or other type, or use of probes with transducers that are movable or displaceable angularly about one or two orthogonal axes and to the longitudinal axis of the probe, i.e. the ultrasound beam transmission and/or propagation direction axis, as is described in detail in the prior art published documents mentioned above.

Although these techniques may be used in imaging applications that require monitoring of a biopsy needle position, they require too long scanning times, and do not allow a real-time operation. In fact, the whole array of section images must be acquired to obtain a set of voxels wherefrom the best field of view for imaging the needle and/or fluid flows and/or the tissue may be selected.

In combination with one or more of the above characteristics, the invention provides the use of a three-dimensional imaging technique as disclosed in Italian patent application SV2000A000027 by the owner hereof, wherein section images are not scanned over the whole surface covered by the probe, but only along lines that intersect a selected image plane, with a predetermined space orientation.

Particularly, according to this three-dimensional scan method, a starting position of the ultrasonic probe is determined, on whose basis a virtual volume is constructed which has such a size as to essentially enclose the whole region under examination. A starting scan plane, having a particular orientation relative to the predetermined volume, is associated to this virtual volume. The personnel selects a section plane within the virtual volume which encloses the region under examination. Based on the indications about the position and size of the virtual volume and on the position of the reference scan plane, the apparatus determines, by a simple geometrical calculation, the projection of the selected image plane on the plane orthogonal to the reference scan plane, and only scans, on the scan planes, the lines that coincide with said projection. As a result, the number of lines to be scanned for each section plane amongst the set of section images which form the three-dimensional image, is drastically reduced. In the best condition, only one line is to be scanned for each section plane. In the worst condition, all the lines must be scanned for each section plane, but with focusing being limited on said image plane.

This three-dimensional imaging technique, in combination with the optimized imaging steps of the method according to the invention, allows to not only optimize imaging parameters, but also to select in real time the best view to image both the needle and the body fluid flow and/or the tissue or the best views to image the needle, the fluid flow and/or possibly the tissue respectively. These views may be displayed separately, e.g. in adjacent or otherwise combined positions.

Obviously, the invention is not limited to the biopsy needle, but may be also applied to any type of similar diagnostic or therapeutic instrument, such as RF, microwave, laser, cryostatic probes or other instruments with similar operating characteristics.

The high flexibility of the apparatus enables to program it for the execution of several different imaging modes. Particularly, besides providing alternate imaging of body fluid flows at the second harmonic and of the needle at the fundamental frequency and/or possibly of the tissues at the fundamental frequency, it is possible to set transmit and receive parameters in such a manner as to perform one or more imaging scans of the needle with parameters optimized therefor and one or more imaging scans of tissues by second harmonic tissue imaging without contrast agents, i.e. tissues are imaged thanks to echo components at the second harmonic of the transmit fundamental frequency.

The versatility of the apparatus according to the invention also allows to develop particular image data combination protocols, to combine the image data obtained with different alternately executed imaging modes, such as B-mode, and Second harmonic imaging. In this case, imaging may be performed regardless of the provision of a biopsy needle. The CPU may be used as a multiplexed imaging controller for the different imaging modes. Also, image data may be displayed separately or in combination by selecting a different color mapping arrangement for each imaging mode. For example, the image data associated to B-Mode imaging may be displayed in a gray scale, whereas the vascular flows imaged with second harmonic imaging methods may be displayed with scales of a single color or with scales of different colors, for also reflecting quantities like direction and/or speed of flow.

In this case, the apparatus and the method of the invention may be applied separately from a biopsy needle or the like, and not for the purpose of imaging it.

With reference to an additional variant embodiment, provided in any combination or under-combination with the characteristics of this invention as described above, the needle or any other diagnostic or therapeutic instrument may be subjected to such a treatment that the material whereof they are made has acoustic impedance adjustment and improved reflection characteristics.

Particularly, this treatment may be a surface treatment, aimed at generating reflection microcavities in the material whereof the needle or therapeutic and/or diagnostic instrument is made, or may consist of an outside coat having predetermined acoustic impedance and reflection characteristics.

The possibilities to treat the material of the needle or of any other instrument are described in U.S. Pat. No. 6,106,473, which is expressly incorporated by reference herein.

In this case, the optimization of transmit, receive and/or processing parameters for the characteristics of the needle or other therapeutic or diagnostic instruments is to be intended as a parameter optimization related to acoustic impedance and reflection characteristics of the treated material.

The invention is not limited to the embodiments illustrated and described herein, but may be greatly varied. Particularly, changes may be made to the structure of the ultrasound apparatus for implementing the method of the invention, wherein the hardware structure may be greatly varied in accordance with the described features. All the above without departure from the guiding principle disclosed above and claimed below.

What is claimed is:

1. A method for ultrasound imaging, including the imaging of a probe during an ultrasound imaging examination, comprising the following steps:
performing one or more imaging scans with ultrasound transmit and receive parameters which are variably adapted for optimized imaging and visualization of said probe and for optimized imaging and visualization of a body in which said probe is inserted, and
for optimized imaging and visualization of body fluid flows, said optimization for imaging and visualization of body fluid flows also comprising the step of injecting contrast agents in a region of said body prior to performing said imaging scans.

2. The method as claimed in claim 1, characterized in that the ultrasound transmit and receive parameters optimized for imaging fluid flows involve the transmission of ultrasound beams at a fundamental frequency and the reception of ultrasound reflected beams at a harmonic frequency, of said transmitted beams.

3. The method as claimed in claim 2, characterized in that said transmitted ultrasound beams have a low mechanical index to avoid or drastically reduce the collapsing effects of said contrast agents.

4. The method as claimed in claim 2, characterized in that said transmitted ultrasound beams have a high mechanical index to cause the collapse of said contrast agents, or an adjustable mechanical index for a controlled collapse of said contrast agents.

5. The method as claimed in claim 1, providing alternate ultrasound imaging with transmit and receive parameters optimized for imaging said probe, with transmit and receive parameters optimized for imaging the tissues of said body under examination, and with transmit and receive parameters optimized for imaging body fluid flows.

6. The method as claimed in claim 1, characterized in that said alternate imaging consists in performing single scans or a group of scans including a succession of a certain number of scans, each scan or each group of scans being performed with different optimization parameters, for imaging said probe, and body fluid flows respectively, and in succession either in a constant or variable order with time.

7. The method as claimed in claim 6, characterized in that said individual scans or groups of scans are performed within the same scan section or distributed over different sections of said body, or a region of said body, under examination.

8. The method as claimed in claim 1, characterized in that the images obtained by said imaging procedures with transmit and receive parameters optimized for said probe and said body fluid flows and for said body tissues are displayed by assigning different colors to the intensity values of the reflected echo beams.

9. The method as claimed in claim 1, further comprising the step of displaying a combined image which is made by overlaying and/or combining images, and is detected with an optimization for said probe, said fluid flows and/or said body tissues.

10. The method as claimed in claim 1, further comprising the step of displaying individual images obtained by optimized imaging of said probe, said body fluid flows and/or said body tissues in separate and adjacent positions or in combined positions, according to any sub-combination between the different images optimized for said probe, for said body fluid flows and/or said tissues.

11. The method as claimed in claim 1, further comprising the steps of providing an imaging procedure for acquiring one or a group of images with a low mechanical index at the second harmonic for imaging body fluid flows; and providing an imaging procedure for acquiring one or a group of images with a low mechanical index and at the fundamental frequency with probe optimized parameters.

12. The method as claimed in claim 1, characterized in that the parameters optimized for probe imaging provide a deformation of the focusing rule according to a steering technique, in which the incidence direction between said ultrasound beam and said probe is substantially orthogonal to said probe.

13. The method as claimed in claim 1, further comprising the steps of providing an imaging procedure for acquiring one or a group of images with a low mechanical index at the second harmonic for imaging body fluid flows; and providing an imaging procedure for acquiring one or a group of images with a high mechanical index at the fundamental frequency with probe optimized parameters.

14. The method as claimed in claim 1, further comprising the steps of providing an imaging procedure for acquiring one or a group of images with a low mechanical index at the second harmonic for imaging body fluid flows; and providing an imaging procedure for acquiring one or a group of images with a high mechanical index at the fundamental frequency with probe optimized parameters; and providing an imaging procedure for acquiring one or more images with a high mechanical index at the fundamental frequency with tissue optimized parameters.

15. The method as claimed in claim 1, further comprising the steps of providing an imaging procedure for acquiring one or a group of images with a low mechanical index at the second harmonic for imaging body fluid flows; and providing an imaging procedure for acquiring one or a group of images with a high or low mechanical index at the fundamental frequency with probe optimized parameters; and providing an imaging procedure for acquiring one or more images with a high mechanical index at the second harmonic frequency with tissue optimized parameters.

16. The method as claimed in claim 1, further comprising the steps of providing an imaging procedure for acquiring one or more images at the second harmonic optimized for imaging body fluid flows; and providing an imaging procedure for acquiring one or more images with a high or low mechanical index at the fundamental or second harmonic frequency, which subtracts two successive reflection echoes determined by two successively fired ultrasound beams with the same parameters for imaging said probe.

17. The method as claimed in claim 1, characterized in that the different imaging procedures with parameters optimized for imaging said probe, said body fluid flows and/or said body tissues are executed alternately, within a predetermined frame rate, or simultaneously to each other, at least as regards the processing of received echoes, there being provided two or three dedicated receiving and processing chains.

18. The method as claimed in claim 1, further providing several imaging procedures for acquiring one or more images with the different parameters optimized for imaging said probe, said body fluid flows and/or said tissues, said procedures being in combination with three-dimensional imaging methods which perform scans of predetermined adjacent section planes to generate a three-dimensional image data matrix in combination with locating the transducers and/or the probe for each scan plane for which a scan has been performed.

19. The method as claimed in claim 1, further comprising the steps of:
transmitting ultrasonic beams generated by transducers into an object volume corresponding to a body under examination or a part thereof;
receiving and storing signals generated by said ultrasonic beams in said object volume;
processing the received signals into image data associated with image dots or lines of a video display;
displaying at least a portion of said image data on said display according to user selected parameters relating to a predetermined image section or projection plane of said volume under examination, the processing of said ultrasound beams and/or said display being predetermined in a targeted manner with reference to a previous selection of an image section or projection plane of the volume under examination to be imaged;
defining a virtual volume coincident with said object body or part thereof or a three-dimensional reference system, provided it has a definite orientation with respect to the imaging planes generated by the ultrasound probe;
selecting the section plane of said object body and/or part thereof along which ultrasound imaging is to be performed;
determining the position-defining coordinates for the dots which form said section plane along which imaging is to be performed, with reference to the virtual volume;

restricting the scanning operation to the region which coincides with said section plane along which imaging is to be performed;

transmitting the transmission signals and receiving the reflected echoes only along such lines of view of the probe which coincide with the surface or the projection slice of the selected section plane along which imaging is to be performed; only processing and displaying the received echo signals;

the execution of the above imaging steps for acquiring one or more images with parameters optimized for imaging said probe and/or optimized for imaging fluid flows and/or optimized for imaging tissues.

20. The method as claimed in claim 1, further providing an alternate and sequential transmission of ultrasound beams with parameters optimized for imaging said probe, said body fluid flows and/or said tissues respectively, said alternate processing of received data deriving from the said parameters of said transmitted ultrasound beams, there being provided a memory in which said parameters for optimized imaging of said probe, said body fluid flows and/or said stationary tissues are stored for user selection.

21. The method as claimed in claim 20, further providing automatic modification of said transmit parameters based on presettable protocols for alternate imaging optimized for said probe and/or said body fluid flows and/or said tissues.

22. The method as claimed in claim 1, further providing that a different or identical number of images to be acquired may be set alternately with the specific optimization for said probe, for said fluid flows and/or said tissues.

23. The method as claimed in claim 22, characterized in that a greater number of images optimized for imaging said probe, said body fluid flow and/or said tissues is acquired for the imaging type which is to have the best image quality.

24. The method as claimed in claim 1, further providing presetting and storage of parameters optimized for imaging said probe and/or said body fluid flows and/or said tissues both with regards to transmitted ultrasound beams and with regard to reflected and received ultrasound beams and/or also with regard to the different image coloring and/or displaying and/or combining modes, and protocols for executing imaging procedures optimized relative to each other and in such a manner that a specific setting of the parameters for controlling the processing and possibly a specific setting of processing, handling and/or combining parameters for images detected in different modes for said probe, said body fluid flows and/or said tissues corresponds to each specific setting of the parameters of transmitted ultrasound beams, univocally related to imaging optimized for said probe, said body fluid flows and/or said tissues.

25. The method as claimed in claim 1, further providing a modulation of intensity of said ultrasound beams within the imaging procedures for said probe, and/or said body fluid flows and/or said tissues.

26. The method as claimed in claim 1, further providing storage of the parameters optimized for imaging said probe, said fluid flows and/or said tissues into a working storage memory which is accessible by the scan control unit and/or by the image processing and/or handling and/or combining unit, with no need to reprogram said units.

27. An apparatus for implementing a method for ultrasonic imaging comprising an ultrasonic probe; means for generating ultrasound beams and for controlling the scan of a body under examination by ultrasound beams; means for receiving and reconstructing image data from said ultrasound beams reflected by said body under examination; and display means, said apparatus further comprising a memory in which the parameters for generating said ultrasound beams and the methods for scanning the body under examination or a part thereof are loaded, said parameters being alternately optimized for imaging said probe and/or body fluid flows and/or body tissues, and means for receiving, reconstructing and processing reflected ultrasound beams deriving from said transmit beams, which operate in relation to the generating parameters and scan modes with said transmitted ultrasound beams.

28. The method of claim 1, wherein said probe comprises a biopsy needle.

29. The method of claim 1, wherein said probe comprises a diagnostic or therapeutic probe of a type including rf, microwave, laser or cryostatic.

30. The apparatus as claimed in claim 27, further comprising a single processing chain for generating said ultrasound beams transmitted toward said body under examination, wherein the optimization of imaging parameters and/or imaging modes is controlled by means provided with a parameter setting memory in which parameters are provided to a scan control unit by a monitoring unit according to predetermined enabling protocols which provide alternate scans with the different parameters.

31. The apparatus as claimed in claim 27, characterized in that it includes one or more receive and processing chains, each dedicated to the simultaneous or sequential handling of the data obtained by any type of optimized imaging parameters.

32. The apparatus as claimed in claim 27, characterized in that it includes a single chain for generating the ultrasound beams to be transmitted and/or for scanning and a single chain for receiving and processing and/or a single chain for handling and/or combining images, which chains are of the controllable type, there being provided a central control unit which is connected to the memories containing the parameters of ultrasound beams transmitted according to the different optimizations for imaging said probe and said body fluid flows and/or said tissues, and to the memories containing the receive and processing modes dedicated to the reflection signals obtained with the particular settings of parameters optimized for imaging said probe and/or said body fluid flows and/or said tissues, and/or to the memories containing the particular image handling and/or image combining settings, as well as to the memories containing the imaging protocols according to the different optimizations and the transmit and receive synchronization chains, and to the memories containing the imaging modes, which means access the memories according to a timed imaging protocol, for optimized imaging and, as a result, control the transmit chain and the receive chain as well as the image handling and combining chain.

33. The apparatus as claimed in claim 27, characterized in that it has a working storage memory in which the optimized parameters are loaded and which working storage memory is directly accessible by the units for controlling the scanning, image processing and reconstructing, and handling and combining processes.

34. A method for ultrasound imaging of a probe during an ultrasound imaging examination, wherein one or more imaging scans are alternately performed with ultrasound transmit and receive parameters which are adapted for optimized imaging and visualization of said probe and one or more imaging scans with ultrasound transmit and receive parameters adapted for optimized imaging and visualization of said body, in which said probe is inserted, characterized in that it includes the step of setting the ultrasound transmit and receive parameters adapted to optimized imaging and display of said body in which said probe is inserted, for second harmonic imaging of tissues, without contrast agents.

35. The method as claimed in claim 34, characterized in that, in order to image the tissues around said probe, echo signals are received and processed with a harmonic of the fundamental frequency, particularly the second harmonic.

36. The method as claimed in claim 34, characterized in that it provides that tissues are imaged by receiving and processing the echoes whose frequencies correspond to a harmonic of the fundamental frequency of the transmitted beams without contrast agents.

37. The apparatus as claimed in claim 27, characterized in that it has a working storage memory which is directly accessible by the scan monitoring units and by the processing units, and in which the parameters for the different optimized imaging scans are loaded.

* * * * *

UNITED STATES PATENT AND TRADEMARK OFFICE
CERTIFICATE OF CORRECTION

| | | |
|---|---|---|
| PATENT NO. | : 6,951,542 B2 | Page 1 of 1 |
| APPLICATION NO. | : 10/266549 | |
| DATED | : October 4, 2005 | |
| INVENTOR(S) | : Barbara Greppi | |

It is certified that error appears in the above-identified patent and that said Letters Patent is hereby corrected as shown below:

On The Title Page, insert item (30) Foreign Priority Claim

-- Foreign Application Priority Data
June 29, 2001   (IT) ................................ SV2001A00025 --

Signed and Sealed this
Tenth Day of May, 2016

Michelle K. Lee
*Director of the United States Patent and Trademark Office*